(12) United States Patent
Amundson et al.

(10) Patent No.: US 6,809,701 B2
(45) Date of Patent: Oct. 26, 2004

(54) CIRCUMFERENTIAL ANTENNA FOR AN IMPLANTABLE MEDICAL DEVICE

(75) Inventors: Mark D. Amundson, Cambridge, MN (US); Jeffrey A. Von Arx, Minneapolis, MN (US); William J. Linder, Golden Valley, MN (US); Prashant Rawat, Saint Paul, MN (US); William R. Mass, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 10/634,233

(22) Filed: Aug. 5, 2003

(65) Prior Publication Data

US 2004/0027306 A1 Feb. 12, 2004

Related U.S. Application Data

(63) Continuation of application No. 10/252,494, filed on Sep. 23, 2002, now Pat. No. 6,614,406, which is a continuation of application No. 09/921,653, filed on Aug. 3, 2001, now Pat. No. 6,456,256.

(51) Int. Cl.$^7$ ................................................ H01Q 1/40
(52) U.S. Cl. ...................... 343/873; 343/741; 128/903; 607/60
(58) Field of Search ................................. 343/741, 742, 343/866, 867, 872, 873, 860; 128/903; 607/32, 36, 60, 61

(56) References Cited

U.S. PATENT DOCUMENTS

| | | | |
|---|---|---|---|
| 4,441,498 A | 4/1984 | Nordling | 128/419 PG |
| 4,519,401 A | 5/1985 | Ko et al. | 118/748 |
| 4,542,535 A | 9/1985 | Brockway et al. | 455/78 |
| 4,562,841 A | 1/1986 | Brockway et al. | 128/419 PG |
| 4,634,294 A | 1/1987 | Christol et al. | 374/170 |
| 4,803,987 A | 2/1989 | Calfee et al. | 128/419 |
| 4,944,299 A | 7/1990 | Silvian | 128/419 PG |
| 5,089,019 A | 2/1992 | Grandjean | 623/3 |
| 5,109,853 A | 5/1992 | Taicher et al. | 128/653.2 |
| 5,113,869 A | 5/1992 | Nappholz et al. | 128/696 |
| 5,314,453 A | 5/1994 | Jeutter | 607/61 |
| 5,342,408 A | 8/1994 | deCoriolis et al. | 607/32 |
| 5,486,200 A | 1/1996 | Lindemans | 607/5 |
| 5,516,285 A | 5/1996 | Yacker et al. | 433/72 |
| 5,535,752 A | 7/1996 | Halperin et al. | 128/670 |
| 5,579,876 A | 12/1996 | Adrian et al. | 188/322.17 |
| 5,598,847 A | 2/1997 | Renger | 128/691 |
| 5,650,759 A * | 7/1997 | Hittman et al. | 333/182 |
| 5,766,232 A | 6/1998 | Grevious et al. | 607/60 |
| 5,807,397 A | 9/1998 | Barreras | 607/61 |
| 5,833,603 A | 11/1998 | Kovacs et al. | 600/317 |
| 5,861,019 A | 1/1999 | Sun et al. | 607/60 |
| 5,904,708 A | 5/1999 | Goedeke | 607/18 |
| 5,919,210 A | 7/1999 | Lurie et al. | 607/3 |
| 6,009,350 A | 12/1999 | Renken | 607/32 |
| 6,115,583 A | 9/2000 | Brummer et al. | 455/41 |
| 6,115,634 A | 9/2000 | Donders et al. | 607/32 |
| 6,115,636 A | 9/2000 | Ryan | 607/60 |
| 6,169,925 B1 | 1/2001 | Villaseca et al. | 607/60 |
| 6,240,317 B1 | 5/2001 | Villaseca et al. | 607/60 |

(List continued on next page.)

FOREIGN PATENT DOCUMENTS

| | | | | |
|---|---|---|---|---|
| EP | 0168640 | 1/1986 | | G01K/1/02 |
| EP | 1050265 | 11/2000 | | A61B/5/00 |

*Primary Examiner*—Tan Ho
(74) *Attorney, Agent, or Firm*—Schwegman, Lundberg, Woessner & Kluth, P.A.

(57) ABSTRACT

An apparatus and method for enabling far-field radio-frequency communications with an implantable medical device in which an antenna is embedded within a dielectric around the periphery of the device. Such a circumferential antenna saves space while still permitting far-field telemetry over a desired range of frequencies.

20 Claims, 3 Drawing Sheets

U.S. PATENT DOCUMENTS

| | | | |
|---|---|---|---|
| 6,263,246 B1 | 7/2001 | Goedeke et al. | 607/60 |
| 6,275,737 B1 * | 8/2001 | Mann | 607/61 |
| 6,309,350 B1 | 10/2001 | VanTassel et al. | 600/300 |
| 6,329,920 B1 * | 12/2001 | Morrison et al. | 340/573.3 |
| 6,427,088 B1 | 7/2002 | Bowman et al. | 607/60 |
| 6,434,429 B1 | 8/2002 | Kraus et al. | 607/60 |
| 6,456,256 B1 | 9/2002 | Amundson et al. | 343/873 |
| 6,470,215 B1 | 10/2002 | Kraus et al. | 607/60 |
| 6,574,509 B1 | 6/2003 | Kraus et al. | 607/60 |
| 6,574,510 B2 * | 6/2003 | Von Arx et al. | 607/60 |
| 6,614,406 B2 * | 9/2003 | Amundson et al. | 343/873 |
| 6,622,043 B1 | 9/2003 | Kraus et al. | 607/27 |
| 6,675,045 B2 * | 1/2004 | Mass et al. | 607/32 |
| 6,687,546 B2 | 2/2004 | Lebel et al. | 607/60 |
| 6,708,065 B2 * | 3/2004 | Von Arx et al. | 607/60 |
| 2001/0047125 A1 | 11/2001 | Quy | 600/300 |
| 2002/0065539 A1 | 5/2002 | Von Arx et al. | 607/60 |

* cited by examiner

CIRCUMFERENTIAL ANTENNA FOR AN IMPLANTABLE MEDICAL DEVICE

CROSS-REFERENCE TO RELATED APPLICATION(S)

This application is a continuation of U.S. patent application Ser. No. 10/252,494, filed on Sep. 23, 2002 now U.S. Pat. No. 6,614,406, which is a continuation of U.S. patent application Ser. No. 09/921,653, filed on Aug. 3, 2001, now issued as U.S. Pat. No. 6,456,256, the specifications of which are incorporated herein by reference.

FIELD OF THE INVENTION

This invention pertains to implantable medical devices such as cardiac pacemakers and implantable cardioverter/defibrillators. In particular, the invention relates to an apparatus and method for enabling radio-frequency telemetry in such devices.

BACKGROUND

Implantable medical devices, including cardiac rhythm management devices such as pacemakers and implantable cardioverter/defibrillators, usually have the capability to communicate data with a device called an external programmer via a radio-frequency telemetry link. A clinician may use such an external programmer to program the operating parameters of an implanted medical device. For example, the pacing mode and other operating characteristics of a pacemaker may be modified after implantation in this manner. Modern implantable devices also include the capability for bidirectional communication so that information can be transmitted to the programmer from the implanted device. Among the data which may be telemetered from an implantable device are various operating parameters and physiological data, the latter either collected in real-time or stored from previous monitoring operations.

Telemetry systems for implantable medical devices utilize radio-frequency energy to enable bidirectional communication between the implantable device and an external programmer. An exemplary telemetry system for an external programmer and a cardiac pacemaker is described in U.S. Pat. No. 4,562,841, issued to Brockway et al. and assigned to Cardiac Pacemakers, Inc., the disclosure of which is incorporated herein by reference. A radio-frequency carrier is modulated with digital information by, for example, amplitude shift keying where the presence or absence of pulses in the signal constitute binary symbols or bits. The external programmer transmits and receives the radio signal with an antenna incorporated into a wand which can be positioned in proximity to the implanted device. The implantable device also generates and receives the radio signal by means of an antenna formed by a wire coil wrapped around the periphery of the inside of the device casing.

In previous telemetry systems, the implantable device and the external programmer communicate by generating and sensing a modulated electromagnetic field in the near-field region with the antennas of the respective devices inductively coupled together. The wand must therefore be in close proximity to the implantable device, typically within a few inches, in order for communications to take place. This requirement is an inconvenience for a clinician and limits the situations in which telemetry can take place.

SUMMARY OF THE INVENTION

The present invention is an apparatus and method for enabling communications with an implantable medical device utilizing far-field electromagnetic radiation. Using far-field radiation allows communications over much greater distances than with inductively coupled antennas. Efficient emission and reception of far-field energy in a desirable frequency range, however, requires an antenna structure with certain minimum dimensions. In accordance with the invention, a wire antenna is embedded in dielectric compartment that wraps around the exterior of the conductive housing of the implantable device in a circumferential orientation. By encapsulating the antenna within the compartment, the antenna is protected from bending or breakage, does not interfere with the device at its implanted site, and requires no special implantation procedure. The dielectric compartment also separates the antenna from the conductive housing and allows the antenna to function as a transmission line antenna.

DETAILED DESCRIPTION

Figure 1A:
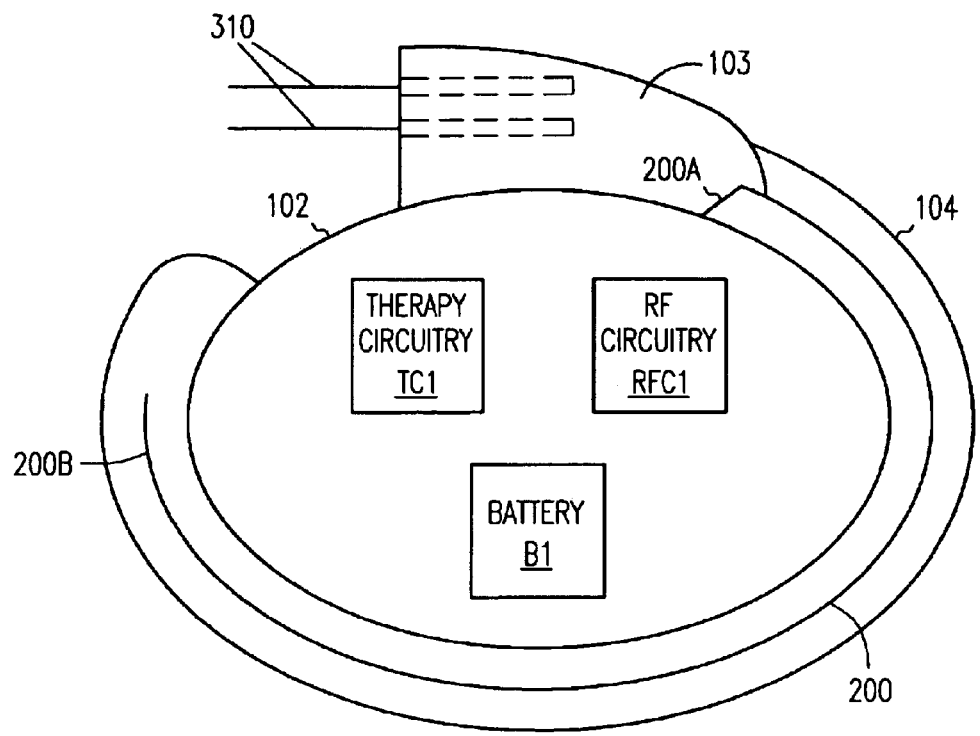
FIGS. 1A and 1B illustrate different implementations of an embedded circumferential antenna.

As noted above, conventional radio-frequency (RF) telemetry systems used for implantable medical devices such as cardiac pacemakers utilize inductive coupling between the antennas of the implantable device and an external programmer in order to transmit and receive RF signals. Because the induction field produced by a transmitting antenna falls off rapidly with distance, such systems require close proximity between the implantable device and a wand antenna of the external programmer in order to work properly, usually on the order of a few inches. The present invention, on the other hand, is an apparatus and method for enabling telemetry with an implantable medical device utilizing far-field radiation. Communication using far-field radiation can take place over much greater distances which makes it more convenient to use an external programmer. Also, the increased communication range makes possible other applications of the telemetry system such as remote monitoring of patients and communication with other types of external devices.

A time-varying electrical current flowing in an antenna produces a corresponding electromagnetic field configuration that propagates through space in the form of electromagnetic waves. The total field configuration produced by an antenna can be decomposed into a far-field component, where the magnitudes of the electric and magnetic fields vary inversely with distance from the antenna, and a near-field component with field magnitudes varying inversely with higher powers of the distance. The field configuration in the immediate vicinity of the antenna is primarily due to the near-field component, also known as the induction field, while the field configuration at greater distances is due solely to the far-field component, also known as the radiation field. The near-field is a reactive field in which energy is stored and retrieved but results in no net energy outflow from the antenna unless a load is present in the field, coupled either inductively or capacitively to the antenna. The far-field, on the other hand, is a radiating field that carries energy away from the antenna regardless of the presence of a load in the field. This energy loss appears to a circuit driving the antenna as a resistive impedance which is known as the radiation resistance. If the frequency of the RF energy used to drive an antenna is such that the wavelength of electromagnetic waves propagating therein is much greater than the length of the antenna, a negligible far-field component is produced. In order for a substantial portion of the energy delivered to the antenna to be emitted as far-field radiation, the wavelength of the driving signal should not be very much larger than the length of the antenna.

An antenna most efficiently radiates energy if the length of the antenna is an integral number of half-wavelengths of the driving signal. A dipole antenna, for example, is a center-driven conductor that has a length equal to half the wavelength of the driving signal. Such a dipole antenna can be made of two lengths of metal arranged end to end with the cable from a transmitter/receiver feeding each length of the dipole in the middle. An efficiently radiating resonant structure is formed if each length of metal in the dipole is a quarter-wavelength long, so that the combined length of the dipole from end to end is a half-wavelength. A shorter antenna can produce a similar field configuration by utilizing a ground plane to reflect electromagnetic waves emitted by the antenna and thereby produce an image field. A monopole antenna is a conductor with a length equal to one-quarter the wavelength of the driving signal situated with respect to a reflecting ground plane so that the total emitted and reflected field configuration resembles that of the dipole antenna. For implantable medical device applications, carrier frequencies between 300 MHz and 1 GHz are most desirable. For example, the carrier signal may be selected to be 1 gigahertz, which corresponds to a wavelength in free space of approximately 32 cm in free space. In free space, a half-wavelength dipole antenna in would optimally be approximately 16 cm long, and a quarter-wavelength monopole antenna would optimally have a length approximately 8 cm with the housing 101 serving as a ground plane. Because the permittivity of body tissues is greater than that of free space, the corresponding optimum dipole and monopole antennas in the human body would be approximately half these lengths. If it is desired to use a lower frequency carrier, even longer antennas must be used.

One way of implementing far-field telemetry in an implantable medical device is to use an antenna that extends from the device housing. The device housing is metallic and forms an electrically shielded compartment for electronic circuitry that provides particular functionality to the device such as cardiac rhythm management, physiological monitoring, drug delivery, or neuromuscular stimulation. The housing also contains circuitry for transmitting and receiving RF communications. The antenna could then take the form of a conductor covered by insulation that extends from the housing and is electrically connected to the RF transmitter/receiver within the housing. The antenna could be any conductive structure capable of efficiently radiating electromagnetic energy well known to those of skill in the art such as a rod, a wire, a patch, or a loop. Wire antennas, however, are simple to manufacture, and are volumetrically efficient. They also tend to have a near isotropic radiation pattern in the horizontal plane with fewer null locations as compared with other types of antennas. This is particularly desirable with a far-field telemetry system in an implantable device since movement of the patient may arbitrarily orient the antenna with respect to the receiving antenna of the external device.

An external wire antenna for an implantable medical device capable of emitting far-field radiation, however, may require special implantation procedures and may also be broken or deformed as a patient moves, resulting in de-tuning. In accordance with the present invention, therefore, the antenna is embedded in a dielectric and contained within a compartment of the implantable device. An example of a suitable dielectric is the polyurethane resin used in the header portion of cardiac rhythm management devices where the therapy leads connect to the device. The compartment could be, for example, within the device header itself or a specialized compartment within the housing having a dielectric window. For reasons of patient comfort, however, it is desirable for implanted devices to be as small as possible, and this constrains the carrier frequencies that can be used if a quarter-wavelength monopole or half-wavelength dipole antenna is to be embedded in a compartment.

A particular embodiment of the invention that minimizes space requirements but still allows for efficient radiation is a wire antenna embedded in a dielectric compartment that wraps around the exterior of the device housing. The wire antenna is thus oriented circumferentially around the periphery of the conductive housing and separated from it by the insulating dielectric. If the wire is held at a fixed distance from the conductive housing by the compartment, the wire exhibits radiation characteristics between a transmission line and a monopole antenna. If the wire diameter is small and the separation between the wire and conductive housing is reasonably distant, the wire thus acts as a transmission line antenna. The antenna is thus a one-piece design integral to the implantable device and permits the antenna to have a longer electrical length. Given the size constraints of implantable devices, an ideal monopole antenna may not be practical at the desired carrier frequency. A lossy transmission line, however, can be made to have radiation characteristics that resemble the performance of a monopole antenna. Although such a transmission line antenna may not be as efficient as a quarter-wavelength monopole, it does offer a balanced compromise between size, efficiency, and radiation pattern.

Figure 1B:
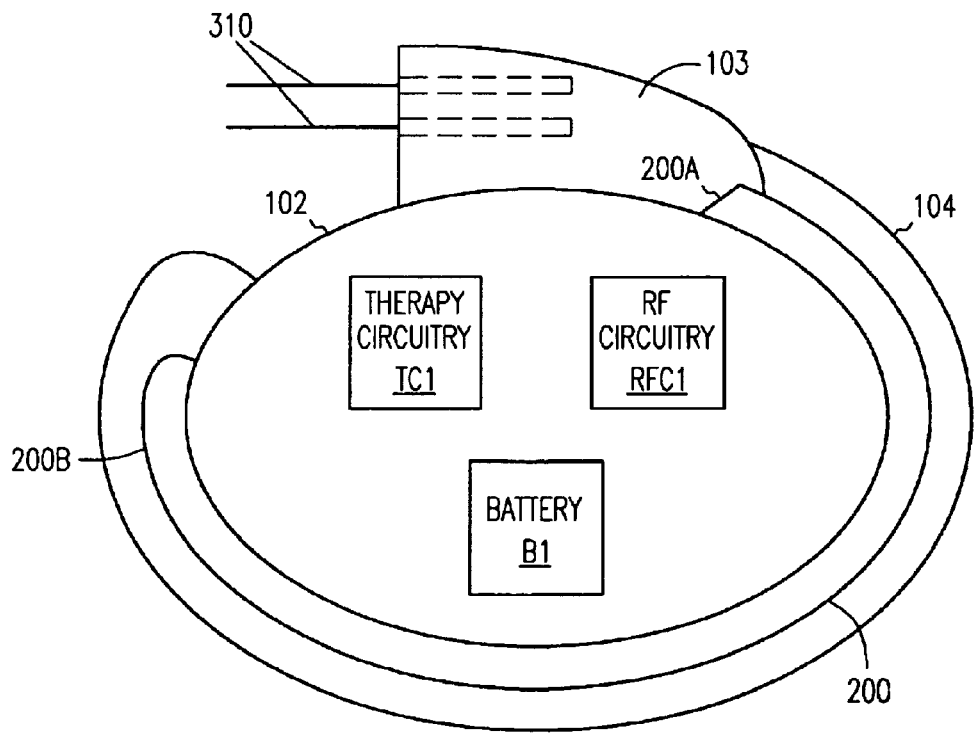
Figure 2A:
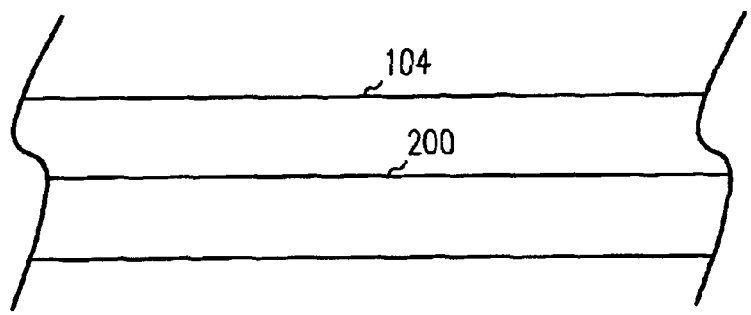
FIGS. 2A and 2B are cross-sectional views of the circumferential compartment.
Figure 2B:
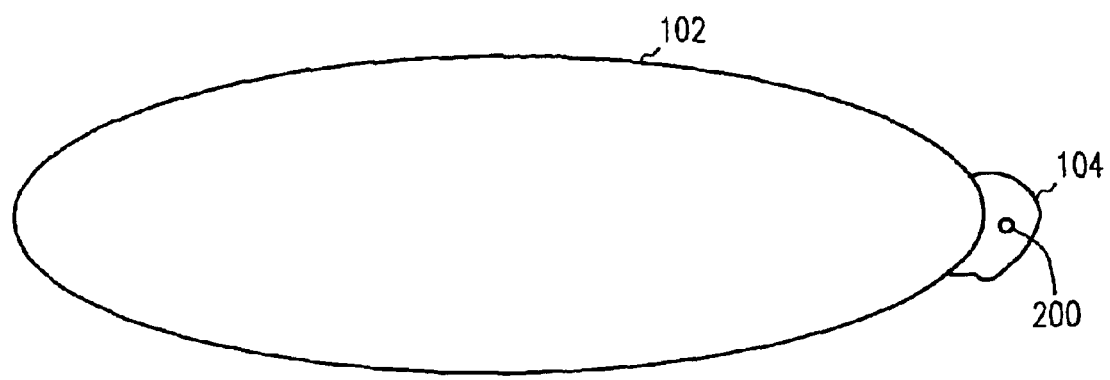

FIGS. 1A and 1B show different embodiments of an exemplary implantable cardiac rhythm management device with a compartmentalized circumferential antenna 200 suitable for radiating and receiving far-field electromagnetic radiation. The device housing 102 is metallic and contains therapy circuitry TC1 for providing particular functionality to the device such as cardiac rhythm management, physiological monitoring, drug delivery, or neuromuscular stimulation as well as circuitry RFC1 for providing RF communications. A battery B1 is used to supply power to the electronic circuitry within the housing. One or more therapy leads 310 are connected to the therapy circuitry contained within the housing by means of a header 103. Each lead 310 is connected to one or more electrodes 311 adapted for disposition within or near the heart. The header 103 is a solid block structure made from a synthetic polymer that has feedthroughs therein for routing electrical connectors between the therapy leads 310 and the therapy circuitry TC1. The antenna compartment 104 is made of dielectric material and extends from the header 103 to wrap circumferentially around a curved portion of the device housing 102 with the antenna 200 embedded therein. The antenna 200 may be constructed of metal wire such as an alloy made of approximately 90% platinum and 10% iridium. Such a material is commonly used for feedthroughs of therapeutic leads and is both mechanically strong and biocompatible. This means that no welding or other means of attachment is required for attaching the antenna to the device and the antenna can be routed from the transmitting and receiving circuitry within the housing through the feedthrough to the dielectric compartment with no interposing connections required. An alternative antenna and feedthrough material is niobium, which has a slightly lower resistivity than the 90% platinum and 10% iridium alloy. In the embodiment shown in FIG. 1A, the wire antenna 200 has a proximal end 200a that exits the device housing through a feedthrough and begins its radiating length around the edge of the device, terminating at the distal end 200b. The embodiment of FIG. 1B is similar except that the distal end 200b of the antenna is shorted to the device housing. FIGS. 2A–B are cross-sections of the dielectric compartment 104 from side and end-on views, respectively, that show the mid-line location of the antenna 200 within the compartment.

A transmission line antenna within a dielectric compartment that is oriented along a surface of the device housing is capacitively connected to the conductive device housing. This includes both the circumferential antenna shown in FIGS. 1A–B as well as alternate designs where the antenna and compartment extend linearly along a relatively flat surface of the device housing. This capacitance along the length of the antenna causes losses that lessen the radiation efficiency of the antenna. These losses become larger as the frequency of the driving signal increases and as the value of capacitance increases. One way to decrease the value of the capacitance is to increase the distance separating the antenna from the device housing, but this necessarily increases the size of the device. The preferred separation distance between the antenna and the housing will be effected by a number of factors, including the dielectric constant of the compartment material and the carrier frequency. In an exemplary implementation, however, it may be desirable that the separation distance between the antenna and housing be on the order of only 1.5 to 2.5 millimeters. Another way to decrease the capacitance without changing the separation distance is to use a compartment material with a lower dielectric constant. The material commonly used as a header material in pacemakers is thermoplastic urethane (tecothane) which has a dielectric constant of about 4.4. If tecothane is used as the compartment material, the capacitance is then four times greater than would be the case if antenna and housing were separated by air and may result in unacceptable losses to the antenna. A material with a lower dielectric constant of only 2.1 to 2.4 is polytetrafluoroethylene (PTFE). Construction of the antenna compartment with PTFE instead of thermoplastic urethane thus increases the radiation efficiency of the antenna by decreasing the capacitance between the antenna and the device housing. Absorption of water by the compartment material also increases its dielectric constant, and PTFE is hydrophobic while tecothane is hydrophilic. Other materials with lower dielectric constants that could be used as a compartment material include expanded polytetrafluoroethylene (ETFE) with a dielectric constant of 2.6, and polyetheretherketone (PEEK) with dielectric constant of 3.6.

Because of the space requirements of implantable devices, the physical length of a compartmentalized antenna on the surface of the device is constrained. Reducing the capacitive loading of an antenna, however, also decreases its effective electrical length, thus compromising the ability to operate at lower frequencies. In order to increase its capacitive loading, the antenna may be coated with a high dielectric material. Coating materials especially suitable for this purpose are oxides of titanium or aluminum.

Figure 3A:
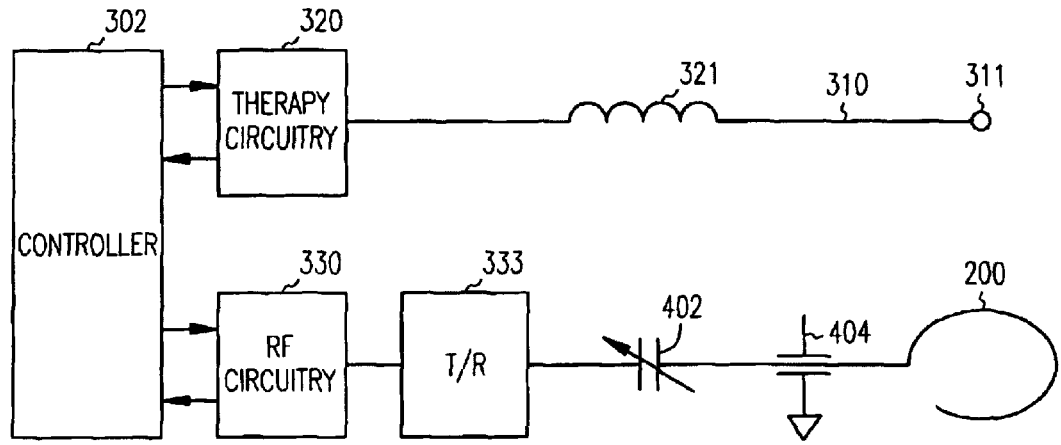
FIGS. 3A and 3B illustrate alternative embodiments for connecting the components of an exemplary cardiac rhythm management device to a circumferential wire antenna.
Figure 3B:
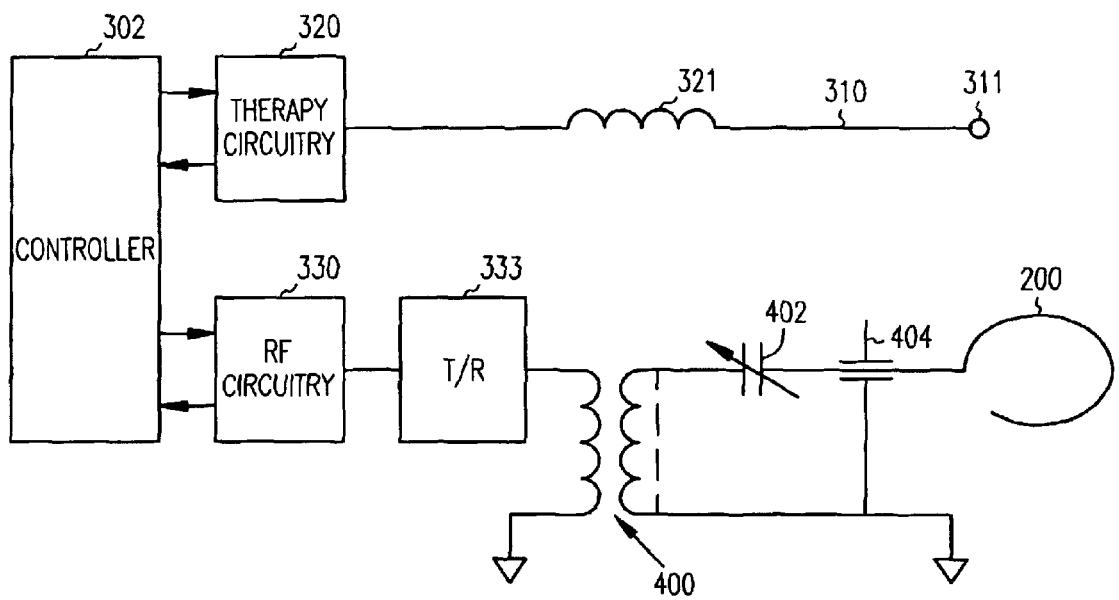

FIGS. 3A–B are block diagrams of an exemplary implantable cardiac rhythm management device showing examples of how a circumferential antenna may be connected and driven. In the figures, only one therapy lead 310 is shown but it should be understood that a cardiac rhythm management device may use two or more such leads. A microprocessor controller 302 controls the operation of the therapy circuitry 320, which includes sensing and stimulus generation circuitry that are connected to electrodes by the therapy leads for control of heart rhythm, and RF drive circuitry 330 for transmitting and receiving a carrier signal at a specified frequency modulated with telemetry data. The conductors of the therapy lead 310 connect to the therapy circuitry 320 through a filter 321 that serves to isolate the circuitry 320 from any RF signals that may be picked up by the lead. The filter 321 may be a low-pass filter or a notch filter such as a choke.

The microprocessor 302 also outputs and receives the data contained in the modulated carrier generated or received by the drive circuitry 330. The RF drive circuitry 330 includes an RF transmitter and receiver that are connected by a transmit/receive switch 333 to the antenna. The conductor that connects the transmit/receive switch to the antenna passes from the interior of the device housing to the exterior where the antenna is located through a feedthrough 404. An antenna tuning circuit may be employed to adjust the impedance of the antenna by loading the antenna with a variable amount of inductance or capacitance. This alters the effective electrical length of the antenna, and hence adjusts its resonance frequency. By matching the antenna impedance to the impedance of the transmitter/receiver at a specified carrier frequency, the reactance of the antenna may be tuned out at that frequency so that the antenna forms a resonant structure and efficiently transmits/receives far-field radiation. In FIG. 3A, the antenna 200 is connected to the transmit/receive switch 333 through a variable tuning capacitor 402. In FIG. 3B, the antenna is connected to the transmit/receive switch through a balun transformer 400 in addition to the tuning capacitor that may allow better impedance matching than when the tuning capacitor alone is used. The balun transformer also electrically isolates the internal circuitry from the device housing which may be advantageous in some pacemakers and defibrillators where the housing or can is utilized as an electrode in delivering pacing or defibrillation pulses.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. An implantable medical device, comprising:
   an implantable housing for containing electronic circuitry;
   an antenna compartment integral to the housing having a dielectric window;
   a wire antenna within the compartment; and,
   circuitry within the housing connected to the antenna for transmitting and receiving a modulated radio-frequency carrier through the dielectric window.

2. The device of claim 1 wherein the dimensions of the antenna are such that a significant portion of radio-frequency energy delivered to the antenna is emitted as far-field radiation.

3. The device of claim 1 wherein the antenna compartment extends from a header for the device having a feedthrough therein for routing the wire antenna between the transmitting and receiving circuitry within the housing and the compartment.

4. The device of claim 1 wherein a distal end of the antenna is shorted to the device housing.

5. The device of claim 1 wherein the housing is constructed of conductive material and further wherein the antenna within the antenna compartment is separated from the conductive housing by a fixed distance on the order of between 1.5 and 2.5 millimeters.

6. The device of claim 1 wherein the wire antenna is coated with an oxide of titanium.

7. The device of claim 1 wherein the wire antenna is coated with an oxide of aluminum.

8. The device of claim 1 wherein the wire antenna is made of an alloy containing approximately 90% platinum and 10% iridium.

9. The device of claim 1 wherein the wire antenna is made of niobium.

10. The device of claim 1 further comprising an antenna tuning circuit for matching the impedance of the antenna to the transmitting/receiving circuitry at a specified frequency of the radio-frequency carrier by loading the antenna with inductance or capacitance.

11. The device of claim 10 wherein the tuning circuit comprises a variable tuning capacitor for adjusting the resonant frequency of the antenna.

12. The device of claim 10 wherein the tuning circuit further comprises a balun transformer.

13. The device of claim 1 wherein the device is a cardiac rhythm management device having rhythm control circuitry electrically connected to one or more electrodes adapted for disposition within or near the heart by one or more therapy leads.

14. A method for constructing an antenna in an implantable device, comprising:

providing an antenna compartment integral to a conductive housing for containing electronic circuitry, wherein the antenna compartment has a dielectric window;

disposing a wire antenna within the antenna compartment; and, connecting circuitry within the housing for transmitting and receiving a modulated radio-frequency carrier to the antenna.

15. The method of claim 14 further comprising extending the antenna compartment from a header for the device having a feedthrough therein for routing the wire antenna between the transmitting and receiving circuitry within the housing and the antenna compartment.

16. The method of claim 14 further comprising shorting a distal end of the antenna to the device housing.

17. The method of claim 14 further comprising disposing the antenna within the antenna compartment so as to be separated from the conductive housing by a fixed distance on the order of between 1.5 and 2.5 millimeters.

18. The method of claim 14 further comprising coating the wire antenna with an oxide of titanium.

19. The method of claim 14 further comprising coating the wire antenna with an oxide of aluminum.

20. The method of claim 14 wherein the wire antenna is made of an alloy containing approximately 90% platinum and 10% iridium.

* * * * *